United States Patent [19]
Chudzik et al.

[11] Patent Number: 5,981,298
[45] Date of Patent: *Nov. 9, 1999

[54] IMMUNOASSAY DEVICE AND METHOD

[75] Inventors: Stephen J. Chudzik; Martha J. Hamilton, both of St. Paul, Minn.

[73] Assignee: Surmodics, Inc., Eden Prairie, Minn.

[ * ] Notice: This patent is subject to a terminal disclaimer.

[21] Appl. No.: 08/860,195

[22] PCT Filed: Dec. 13, 1995

[86] PCT No.: PCT/US95/16333

§ 371 Date: Sep. 30, 1997

§ 102(e) Date: Sep. 30, 1997

[87] PCT Pub. No.: WO96/18904

PCT Pub. Date: Jun. 20, 1996

[51] Int. Cl.[6] .................................................. G01N 33/558
[52] U.S. Cl. ............................ 436/514; 422/55; 422/56; 422/57; 422/58; 422/61; 435/7.92; 435/7.93; 435/287.1; 435/287.2; 435/287.7; 435/810; 435/970; 435/973; 436/164; 436/169; 436/518; 436/524; 436/528; 436/530; 436/805; 436/810; 436/815; 436/816; 436/901
[58] Field of Search ................................. 422/55–58, 61; 435/7.92, 7.93, 287.1, 287.2, 287.7, 810, 970, 973; 436/514, 518, 524, 528, 530, 164, 169, 805, 810, 815, 816, 901

[56] References Cited

U.S. PATENT DOCUMENTS

| 4,270,920 | 6/1981 | Kondo et al. | 435/22 |
| 4,959,307 | 9/1990 | Olson | 422/56 |
| 5,238,652 | 8/1993 | Sun et al. | 422/61 |
| 5,252,496 | 10/1993 | Kang et al. | 436/529 |
| 5,424,220 | 6/1995 | Goerlach-Graw et al. | 436/805 |
| 5,707,818 | 1/1998 | Chudzik et al. | 435/7.93 |

FOREIGN PATENT DOCUMENTS

| 2239313 | 6/1991 | United Kingdom | 422/56 |

Primary Examiner—Christopher L. Chin
Attorney, Agent, or Firm—Fredrikson & Byron, P.A.

[57] ABSTRACT

A device and related method for performing one or more immunoassays to detect the presence of respective analytes in a sample. The device involves the use of a unitary bibulous material providing one or more flow paths having a common origin site and a plurality of respective reagent zones providing the reagents necessary for performing a visual readout, competitive immunoassay for the presence of the respective analyte.

17 Claims, 1 Drawing Sheet

IMMUNOASSAY DEVICE AND METHOD

TECHNICAL FIELD

The present invention relates to the field of diagnostic immunoassays and related devices for carrying out such assays. In another aspect, the invention relates to assays for analytes such as drugs of abuse or their metabolites. In another aspect, the invention relates to devices or means for simultaneously carrying out multiple assays for different analytes within a single sample.

BACKGROUND OF THE INVENTION

The use of analytical assays, including those used to determine the presence of drugs of abuse, has grown rapidly over the past decade. By 1993, the U.S. drug-testing market, alone, was estimated to be at least $500M. The drug-testing industry is poised for further growth as a result of new federal U.S. regulations that will significantly increase the number of workers subject to testing for drug and alcohol abuse.

At present, most drug testing involves sample collection followed by instrument-based "wet chemistry" laboratory analysis. However, the on-site, or "point of care" market has been growing rapidly over the past two years. Although no current figures are available, the market for non-instrumented immunoassay-based drugs of abuse test kits appears to be growing at the rate of 20–40% per year.

Currently, there are a number of single analyte immunoassay-based drugs of abuse diagnostic tests on the market. These include tests produced by Roche Diagnostic Systems, Hansen Hong Biomedical Co. Ltd., Drug Screening Systems, Editek, Inc., Hycor Biomedical, U.S. Drug Testing Inc., Thermedics Detection, Inc., and Fingerprint Biotek. Such devices generally work well for situations in which a specific drug is suspected. In many cases, however, such as in emergency room settings, it would be particularly desireable to have a rapid, self-performing assay for one or more drugs that may be present in a given patient.

A variety of assay kits have been described having the capability to perform diagnostic assays. For instance, a series of patents issued to Olson (U.S. Pat. Nos. 4,959,307; 4,963,468; 5,085,987; and 5,085,988) relate to an immunoseparating strip having a bibulous material, a nondiffusively bound first receptor, and a nondiffusively bound second receptor. In each embodiment, however, the method of using the device requires the first step of preparing a separate test solution containing the sample, antibody for the analyte, and a conjugate of analyte and a label. Once formed, the competitive reaction progresses to the desired extent in the solution phase. The solution is then transferred by the user to the contact portion of the analytical device, where it begins its flow along the path. (See, e.g., the U.S. Pat. No. '987, col. 13, lines 35–38 and col 20, lines 10–11.)

Others have disclosed the use of kits capable of performing two or more assays, including multi-analyte on-site formats. A kit available from Biosite ("Triage" brand), is said to allow the differential detection of the presence of several common drugs of abuse in a single urine or serum sample. See, for example, Buechler, et al, *Clin. Chem.* 38(9):1678–1684 (1992). At least one drawback of this device is the need to separately add sample to a region containing lyophilized reagents, where it is left for a period of time (e.g, 10 minutes), in order to allow the sample to reconstitute and equilibrate with the reagents.

This and other single and multi-analyte test kits currently on the market have several drawbacks. Present formats tend to be quite complex, with specific affinity constants playing a key role in the competitive binding reactions. Moreover, the formats can suffer from false results if the patient is on high doses of the analyte drug. Also, present formats typically require exact reagent concentrations (i.e., ratios of analyte to anti-analyte), which can be compromised if one member of the ligand-receptor pair begins to deteriorate.

Particularly troublesome are kits that rely on the use of an immobilized antibody or binding reagent, where the amount of this reagent needs to be rigidly controlled. The binding capacity of immobilized receptors can be highly dependent on the particular immobilization methods and conditions. This dependence causes the manufacture of such assays to be unpredictable and difficult to reproduce. Shelf life stability can be affected as well.

What is clearly needed is an analyte test kit that can be used for a number of different drugs of abuse, and particularly one that can be simultaneously used to perform a plurality of assays, in a manner that is easier to manufacture and simple and reliable in use.

SUMMARY OF THE INVENTION

Figure 1:
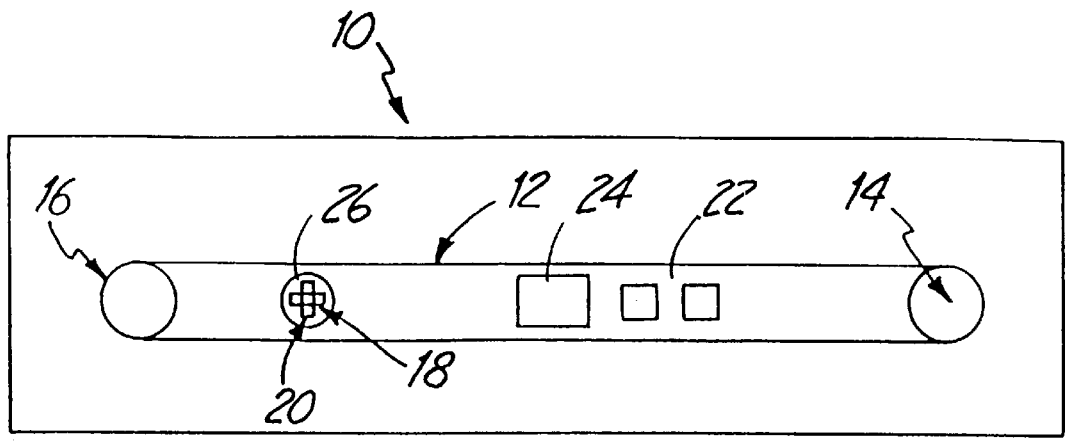
FIG. 1 depicts a diagram of a preferred embodiment of the present invention, having a single analyte, immunoassay-based on-site test format.

The present invention provides a device and related method for performing one or more competitive immunoassays to detect the presence of respective analytes in a sample. The device can be provided as a unitary device, i.e., in which each of the steps and reagents are self-contained on the device. Preferably, each of the steps are self-performing, that is they proceed autonomously upon the application of a sample. In a particularly preferred embodiment, once the sample has been applied to the device, the entire assay (including competitive reaction), progress solely by steps that involve capillary flow from each site or zone to the next. As a result, such a device can be used without the need to separately perform a competitive assay reaction in a solution, or physically transfer the solution in a non-capillary manner to a separate device or zone.

In a preferred embodiment, the device comprises a bibulous material providing one or more flow paths, each flow path comprising:

(a) an origin site for the application of a fluid sample, (b) a plurality of reagent zones emanating from the origin site and providing the reagents necessary for performing a visual readout, competitive immunoassay for the presence of the respective analyte, the zones comprising, in order and in the direction of flow:

(i) a competition zone in fluid communication with the origin site and comprising a detectable analyte-conjugate and binding partner for the analyte, both being diffusively positioned in such a manner that free analyte present in the sample is capable of binding to the binding partner in a competitive manner with the analyte-conjugate;

(ii) a retention zone in latent fluid communication with the competition zone and comprising an excess amount of a nondiffusively bound capture reagent capable of binding to free or bound binding partner in order to remove it from continued flow in the flow path; and (iii) a readout zone in fluid communication with the retention zone and comprising nondiffusively bound receptor capable of binding to analyte-conjugate, but not to unconjugated analyte, in a detectable manner.

In the course of using a device as described above, the presence of increasing amounts of free analyte in a sample corresponds with decreased binding of analyte-conjugate to the binding partner. In turn, an increased amount of free analyte-conjugate is able to continue down the flow path. Ultimately, the free analyte-conjugate becomes nondiffusively bound to a corresponding binding partner in the readout zone, and is there detected in order to provide a positive indication of the presence of analyte in the original sample.

In a preferred embodiment the device and method can be used to simultaneously perform a plurality of immunoassays to detect the presence of respective analytes in a sample. In such a preferred "multi-analyte" embodiment, the device comprises a bibulous material providing one or more flow paths, each flow path comprising:

(a) a common origin site on the bibulous material for the simultaneous application of a fluid sample, (b) a plurality of respective reagent zones in active or latent fluid communication with the origin, the reagent zones of each flow path providing the reagents necessary for performing a visual readout, competitive immunoassay for the presence of the respective analyte, the zones for each flow path comprising, in order and in the direction of flow:

(i) a competition zone in fluid communication with the origin and comprising a detectable analyte-conjugate and binding partner for the respective analyte, both the conjugate and binding partner being diffusively positioned in such a manner that any free analyte present in the sample is capable of binding to the binding partner in a competitive manner with the analyte-conjugate;

(ii) a retention zone in latent fluid communication with a respective competition zone and comprising an excess amount of a nondiffusively bound capture reagent capable of binding to free or bound binding partner in order to remove it from continued flow in the flow path; and (iii) a readout zone in fluid communication with a respective retention zone, and comprising nondiffusively bound receptor capable of binding to analyte-conjugate, but not to unconjugated analyte, in a detectable manner.

The flow paths preferably further each comprise one or more positive and/or negative procedural control zones and reagents. In one preferred embodiment, the device further comprises a terminal site downstream from the sequential reagent zones and comprising an indicator reagent for confirming the completion of the respective assay.

In a particularly preferred embodiment, the device comprises an inert holder comprising top and bottom portions for supporting the bibulous material, the top portion providing an opening for fluid sample access to the common origin, as well as openings for viewing the respective readout and terminal indicator sites along each flow path.

In one embodiment, the flow paths for a plurality of assays can be provided in an overlapping and/or side-by-side manner, and in the same direction along the bibulous material. In an alternative embodiment, the device provides a separate, discrete flow path for each analyte, the flow paths being positioned to extend in a radial direction from the common origin.

In a particularly preferred embodiment, the present invention provides a multi-analyte assay capable of differentially detecting the presence of one to four drug(s) in a single sample of urine or serum. Such analytes include tetrahydrocannabinol (THC), cocaine, opiates, and amphetamines, which are detected without interference from the other analytes.

DETAILED DESCRIPTION

In the present specification, the following words and phrases will have the meaning ascribed to them:

"zone" will refer to a discrete situs containing one or more reagents and positioned along the flow path of a particular assay, each zone or situs having a surface area less than that of the bibulous material;

"downstream", as applied to zones, will refer to a zone that is flowably separated from the preceding zone, and in the direction of flow of a sample. In a typical embodiment, for instance, each zone will be on the order of one or more millimeters from each other. Additionally, there may be two or more discrete regions within zones, such as the regions carrying analyte-conjugate and binding partner, respectively in the competition zone. Alternatively, with non-interfering reagents, zones and/or regions within zones may occasionally be positioned in an overlapping configuration with preceding and/or following zones.

"unitary", as applied to the bibulous material, means that a single aqueous sample can be added to the origin and progress by active or latent capillary flow through each of the zones along a respective flow path. "Bibulous", in turn, refers to a material, or combination of materials, sufficient to permit the capillary flow of sample from the origin and through each reagent zone.

"simultaneous" will mean that each of a plurality of assays on a multi-analyte device are capable of being performed at substantially the same time and by the application of a single sample to the origin.

"competitive" will mean that the amount of analyte-conjugate that becomes bound to free binding partner is dependent upon and related to the presence or absence of analyte in the sample.

"nondiffusively bound" will be used interchangeably with the word "immobilized" to describe reagents that are stably retained in a particular zone under conditions of use.

The present invention provides a device and method for simultaneously performing one or more immunoassays to detect the presence of respective analytes in a sample. Suitable analytes include those capable of being provided in the form of a conjugate. Alternatively, the analyte can be in the form of a derivative or metabolite of the compound of interest.

Generally, an analyte is any compound to be detected that is capable of being bound by a receptor, and capable of being recovered in synthetic and/or purified form sufficient to allow it to be conjugated and used in a competitive assay with sample analyte and the receptor. These compounds include mono-epitopic analytes of relatively small molecular weight (e.g., about 100 to 2000), and poly-epitopic antigens of larger molecular weight (e.g., greater than about 2000). Representative analytes are those described, for instance, in U.S. Pat. Nos. 4,299,916 and 4,275,149, the disclosures of both of which are incorporated herein by reference.

Examples of suitable analytes include, but are not limited to, pesticides and their metabolites and derivatives (e.g., polyhalogenated biphenyls, phosphate esters, thiophosphates, carbamates, polyhalogenated sulfonamides), and drugs and their metabolites and derivatives (e.g., alkaloids, steroids, lactams, aminoalkylbenzenes, benzheterocyclics, purines, vitamins, antibiotics, nucleosides and nucleotides, drugs derived from marijuana, and miscellaneous drugs).

The device and method of the present invention can be used with any suitable sample. Generally, and preferably, the sample is an aqueous one that is obtained directly from the source (e.g., urine or blood). Alternatively, the sample can be prepared by mixing or extracting a non-aqueous sample (e.g., tissue) with an aqueous solvent (e.g., buffered solution). Generally, the sample is any substance suspected of containing the compound or compounds of interest. This includes the analysis of ground water for contaminants, the analysis of agricultural products for naturally occurring toxic agents such as aflatoxin, and the like.

Occasionally, analyses of this type will require an extraction step in which a sample is mixed with a liquid extraction media which can be aqueous, organic, or an aqueous/organic mixture. Upon extraction of the material of interest, the extracting solution itself can be used as the sample and can be evaluated directly or concentrated, diluted, evaporated, and reconstituted, etc. before evaluation in the instant device.

Additional examples of evaluations requiring extraction include pesticide residues, bacterial metabolites or other contaminants in meat or seafood, and herbicide residues or other pollutants in soil samples.

A preferred device of this invention comprises a unitary bibulous material providing one or more flow paths. Preferably, although not necessarily, the bibulous material will actually be provided in the form of a single, integral material. Alternatively, the bibulous can formed by overlapping or abutting otherwise discrete materials. Examples of suitable bibulous materials include (nitrocellulose membranes, nylon membranes, or other commercially available membranes).

Bibulous materials useful in the instant device include porous materials that are susceptible to being traversed by an aqueous medium in response to capillary force. Such materials are generally hydrophilic or are capable of being rendered hydrophilic and include inorganic powders, such as silica and alumina; natural polymeric materials particularly cellulosic materials such as filter paper, chromatographic paper and the like; synthetic or modified naturally occurring polymers such as nitrocellulose, cellulose acetate, poly (vinyl chloride), polyacrylamide, crosslinked dextran, agarose, etc.; either used alone or in conjunction with other materials. A preferred bibulous material includes glass fiber filter paper. The bibulous material can be attached to a support, or may provide its own support. The bibulous material may contain functional groups, or be capable of being functionalized to permit covalent bonding or receptors to other moieties.

When two or more flow paths are employed in a single device, preferably each path comprises a common origin site on the bibulous material for the simultaneous application of a fluid sample. As can be seen, the origin is "common" in that the application of a single sample serves to begin the flow of sample simultaneously in each flow path.

Each flow path in a device of the present invention further comprises a plurality of respective reagent zones at or downstream from the origin site. The reagent zones of each immunoassay provide the reagents necessary for performing a visual readout, competitive immunoassay for the presence of the respective analyte. In a preferred embodiment, the reagent zones provide each of the reagents necessary, i.e., without having to physically remove and reapply reagents (e.g., using a pipet) along the path or in the course of the assay.

The zones of a particular flow path comprise, in the order and direction of flow, a competition zone comprising analyte-conjugate and binding partner for the analyte, both being diffusively positioned in such a manner that any free analyte present in the sample is capable of binding to the binding partner in a competitive manner with the analyte conjugate.

The competition zone can itself serve as the origin site for the application of sample, or it can be downstream from the origin itself. Additionally, the various reagents present in the competition zone can be staggered or arranged in any suitable manner, in order to alter or affect the kinetics of the competition reaction.

For instance, the binding partner can be positioned upstream of the analyte conjugate, in order to allow the analyte to react with the binding partner before the binding partner is exposed to the analyte conjugate. This approach will provide the analyte with a competitive advantage over the conjugate for binding sites on the binding partner. In turn, this approach can be used to increase the sensitivity of detection for a particular analyte.

The binding partner is preferably a receptor for the analyte. A receptor is any compound or composition capable of recognizing a particular spatial and polar organization of the analyte of interest. Illustrative receptors include naturally occurring receptors; e.g., antibodies, enzymes, lectins, and the like. A preferred receptor for the analyte is an antibody to the analyte. An antibody is an immunoglobulin or derivative or fragment thereof having an area on the surface or in a cavity which specifically binds to and is thereby defined as complimentary with a particular spatial and polar organization of another molecule. The antibody can be monoclonal or polyclonal, and can be prepared by techniques that are well known in the art, such as immunization of a host and collection or sera or hybrid cell line technology.

Alternatively, the binding reagent can itself take the form of a complex of molecules, for instance a complex of a first antibody for the analyte and second antibody specific for the first antibody. The components of such a complex can be separately provided either in the competition zone and/or at any suitable location leading to the retention zone. Such complexes can be useful, for instance, in improving the removal of binding reagent in the retention zone by increasing its size or affinity for the capture reagent.

The analyte-conjugate is generally provided in the form of a label or tracer, for example a catalyst, usually an enzyme, conjugated to the analyte. A label can be any molecule or system of molecules bound or conjugated to the analyte that is capable of producing a perceptible signal. A preferred label consists of colloidal metal particles, or sol particles that are colored. Those skilled in the art will recognize that many elements are capable of functioning as a label, including, without limitation, radionuclides, fluorescent species, phosphorescent species, chemiluminescent materials, dyes, enzymes, sol particles, colored polymeric materials, and the like. Based upon the known binding kinetics of the monoclonal anti-drug antibodies, standard techniques can be used to prepare drug conjugates having the correct epitope available for antibody binding.

A flow path further comprises a retention zone in latent fluid communication with the competition zone. By "latent fluid communication" it is meant that the fluid communication between the competition zone and retention zone can be sufficiently delayed, and/or the reaction rate sufficiently increased, in order to allow the competition reaction to progress to a desired extent. In addition to increasing the reaction time within the competition zone, the extent of reaction can be improved by other means as well, such as by elevating the temperature of the binding reaction and/or by improving the mixing characteristics of the reagents (e.g., by effervescence).

The delay means for achieving latent capillary flow can be of a passive nature (i.e., occurring automatically in the course of use), or of an active nature (e.g., requiring some act on the part of the user). Given the present description, those skilled in the art will appreciate the manner in which delay means can be provided and used in a device of the present invention. See, for instance, PCT application Nos. WO 92/21434 and WO 93/24231, the disclosures of which are incorporated herein by reference.

In a suitable approach, the residence time of the solution in the competition zone is increased by configuring the respective competition and retention zones (and/or an interface between them) in such a manner that the flow of solution from the competition zone is controllably delayed. Examples of suitable delay means include, but are not limited to, the use of a dissolvable barrier, a permeable physical barrier, or an expandable bridging material.

For example, a porous or dissolvable barrier can be interspersed between the zones in order to allow the solution to reside in the competition zone for a sufficient period of time before the barrier is itself permeated or dissolved. Similarly, the capillary flow path itself can be made to take a tortuous route between the zones, thereby increasing the effective reaction time for the assay. As yet another example, a hydratable, expandable (e.g., sponge-like) material can be employed in the competition zone, in such a manner that the material is initially not in physical contact with the retention zone. Upon hydration with the test solution, and in the course of allowing the competitive reaction to occur, the material can expand or swell to a point where it makes physical contact and permits fluid communication with the retention zone.

In an alternative embodiment, the latent capillary flow between the competition and retention zones can be actively initiated by the user, e.g., by manipulating or releasing a barrier between zones, forming a capillary bridge between them, or physically placing (e.g., pinching) zones together. See, for instance, U.S. Pat. No. 4,826,759, the disclosure of which is incorporated herein by reference.

The retention zone comprises an excess amount of a nondiffusively bound capture reagent capable of binding to free or bound binding partner in order to remove it from continued flow in the flow path. This capture reagent is a typically a receptor capable of binding to the binding partner. A preferred capture reagent is an antibody capable of binding to the binding partner.

Since the binding partner is preferably an antibody to the analyte, the capture reagent is preferentially an antibody capable of binding to the antibody for the analyte. It can be, for example, an antibody raised in a different species than that used to raise the antibody for the analyte. The capture reagent can also be a receptor, such as protein A, which binds to a particular site on the immunoglobulin molecule. In another embodiment, the binding partner can be coupled to a molecule, such as biotin, and the capture reagent can be specific for such a molecule, for example, antibiotin or avidin.

The approach of the present invention provides a particular advantage over many conventional assays employing immobilized receptors. As described above, the binding capacity of such immobilized receptors can be dependent upon the immobilization methods and conditions, such that the manufacture of such assays is unpredictable and difficult to reproduce. In the present invention, the immobilized capture reagent can be present in an excess amount, thus permitting the development of an assay with predictable performance characteristics.

The immobilization of capture reagent is sufficiently stable, in order to prevent the dissociation of reagent from the material, which in turn could lead to false results. As a further safeguard against error caused by disassociated capture reagent, those skilled in the art will appreciate the manner in which an additional reagent can be employed in order to itself bind and retain disassociated capture reagent. One suitable approach involves the use of a second retention zone, e.g, at or between the first retention zone and the readout zone, having immobilized second capture reagent specific for the first capture reagent (i.e., the capture reagent provided in the retention zone).

Lastly, a flow path further comprises a readout zone comprising nondiffusively bound receptor capable of binding to analyte-conjugate but not to unconjugated analyte in a detectable manner.

The nondiffusively bound receptor is capable of binding to the analyte-conjugate, but not to the analyte alone. This receptor binds then, either to the label portion of the conjugate, or to an additional moiety provided by the conjugate (e.g., by virtue of the binding of analyte and label) but absent from the analyte alone. A preferred nondiffusively bound receptor is an antibody capable of binding to the spacer moiety that is used to conjugate the analyte to the label.

In a particularly preferred embodiment, the readout is provided in the form of the completion of a plus ("+") sign indicating the presence of analyte. In such an embodiment, the minus ("−") portion of the readout can be provided by any suitable means.

In one embodiment, the minus portion is provided by the use of additional reagents positioned along the flow path. For instance, a detectable conjugate is positioned along the flow path, and preferably at the origin itself. The minus portion of the readout can be provided in the form of a nondiffusively bound antibody to the detectable conjugate. For example, when a conjugate of gold-KLH is present in diffusive form, with a nondiffusively bound anti-KLH antibody forming the minus portion of the readout zone.

Lastly, the flow path preferably further comprises a terminal site downstream from the sequential reagent zones and comprising an indicator reagent for confirming the completion of the respective assay. The indicator reagent is typically a material that is sensitive to the presence of the sample. It is generally a material that will change color in response to the presence of some moiety in the sample solution. Examples of such a reagent include pH indicator dyes, dyes sensitive to the presence of proteins, and dyes sensitive to hydration states.

The device of the present invention can be of any suitable form and dimensions in order to achieve the desired purpose. In a preferred embodiment, the device is provided in the form of an inert holder comprising top and bottom portions for supporting the bibulous material, the top portion providing an opening for fluid sample access to the common origin, as well as openings for viewing the respective readout and terminal indicator sites along each flow path.

The manufacture of a typical design of the present test format will be described with reference to the Drawing, including FIG. 1 (single analyte format) and FIG. 2 (multianalyte format). To the user, the test of FIG. 2 would appear as a single test device 10 having paths 12 that emanate and readout in each of four directions. Paths 12 each comprise a competition zone 22 (as shown, having discrete regions therein for analyte-conjugate and first binding partner, respectively), retention zone 24 and readout zone 26. The sample is added to the center well 14, and the test would be complete when the four completion indicator windows 16 change color. If the assay is operating properly, the negative portion 18 of the sign appears as a color change for each of the analytes. If the patient is drug positive for any of the analytes, then the respective plus portion of the readout sign 20 will appear as well.

Figure 2:
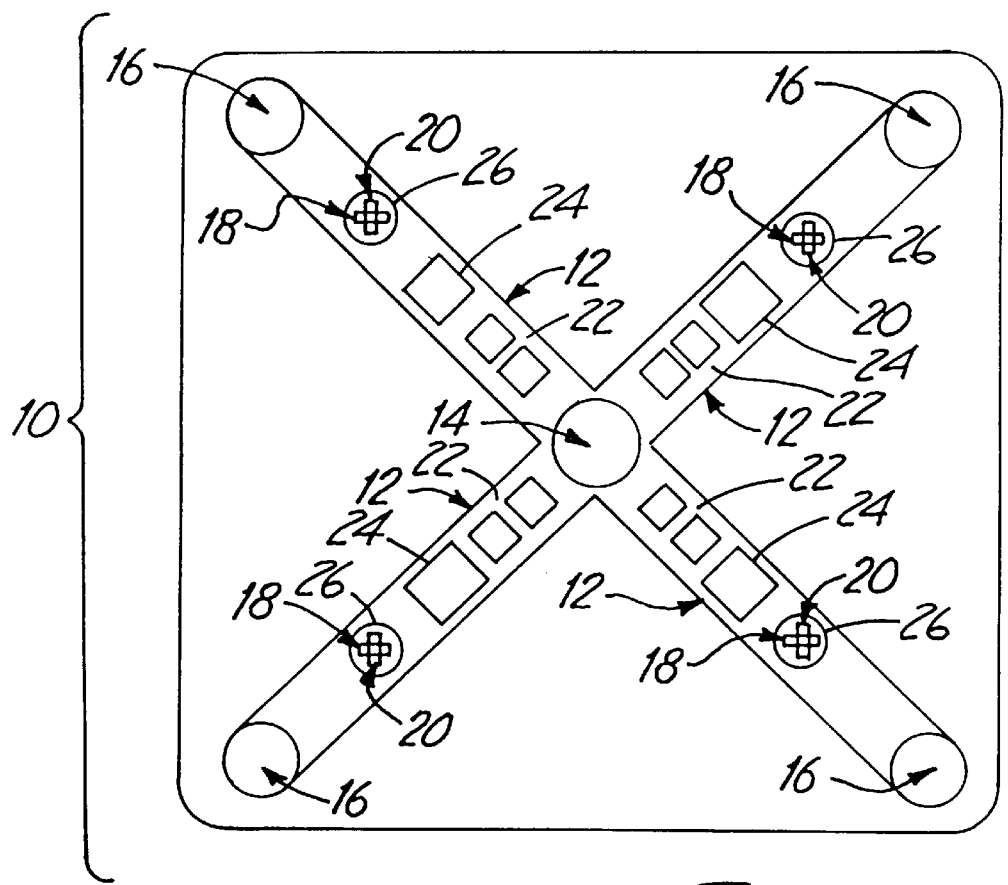
FIG. 2 depicts a diagram of a preferred embodiment of the present invention, having a multiple analyte, immunoassay-based on-site test format.

The devices of FIGS. 1 and 2 show a preferred format for the detection of a single analyte or a plurality of analytes, respectively. Such devices can be prepared and used in the following manner.

Gold-KLH. Keyhole limpit hemocyanin ("KLH") and colloidal gold are obtained from a variety of commercial sources, and conjugated according to standard methods.

Gold-ovalbumin-drugs. Ovalbumin is obtained from a commercial source and coupled to the desired analyte as well as to colloidal gold. Labeling of the carrier protein with colloidal gold is performed by standard methods. Reaction conditions are monitored in order to ensure that the colloidal gold does not interfere with the binding reaction of drug hapten to anti-drug antibody. Similar chemical methods are used for preparing conjugates for THC (marijuana), benzoylecgonine (cocaine), opiates (morphine, morphine glucuronide), amphetamine (amphetamine and methamphetamine).

Nondiffusively bound reagents. Reagents can be immobilized to the bibulous material via any suitable technique as will be apparent to those skilled in the art. Direct attachment methods include nondiffusive adsorption, nondiffusive absorption, attachment to microparticles that are themselves entrapped in the appropriate position, and covalent binding, such as by use of cyanogen bromide, carbonyl diimidazole, or glutaraldehyde. "Nondiffusive", as used in this respect, means that the reagent is sufficiently stable in its position under the conditions of the assay.

Diffusively positioned reagents. Conventional methods are employed for impregnating substrates such as paper with dry chemistry biomolecules. These methods are useful for: 1) optimizing substrate capacity; 2) optimizing the wettability of dried reagents; and 3) increasing the stability of dried reagents.

Indicator Strip. Conventional methods are employed for the preparation of a terminal indicator, for instance, by the use of a pH indicator that will change color when urine is present.

In one embodiment of the device, the diffusively positioned reagents are applied to the competition zone in the appropriate concentrations such that a visibly perceptible signal is generated in the readout zone only when the sample applied to the origin site contains analyte at or above a predetermined concentration. When multiple analytes are being detected from the same sample this predetermined concentration can be different for each analyte.

The operation of the device can be evaluated, for instance, by preparing spiked single drug samples in buffers, using varying concentrations of each drug. Limited cross-reactivity should be tested against other abused substances as well as various common prescription drugs. Spiked multi-drug samples are also tested, with particular emphasis on signal generation and possible signal interference. Signal generation can be "scored" visually against a standard color chart.

In one embodiment, normal human urine is spiked with varying doses of the four drugs of abuse. A total of five sources are used. Evaluation includes comparison of: 1) visually scored signal generation; 2) time for test completion; and 3) the presence of non-specific binding.

The method of the present invention comprises the steps of providing a device of the type described above comprising a bibulous material in the following manner, and:

(a) applying an aqueous sample to the bibulous material at a the origin site of one or more flow paths, (b) allowing the sample to simultaneously flow through each flow path and sequentially through a plurality of respective reagent zones providing the reagents necessary for performing a visual readout, competitive immunoassay for the presence of the respective analyte, the zones comprising, in order and in the direction of flow:

(i) a competition zone in fluid communication with the origin site and comprising a detectable analyte-conjugate and binding partner for the analyte, both being diffusively positioned in such a manner that any free analyte present in the sample is capable of binding to the binding partner in a competitive manner with the analyte conjugate;

(ii) a retention zone in latent fluid communication with the competition zone and comprising an excess amount of a nondiffusively bound capture reagent capable of binding to free or bound binding partner in order to remove it from continued flow in the flow path; and (iii) a readout zone in fluid communication with the retention zone and comprising nondiffusively bound receptor capable of binding to analyte-conjugate but not to unconjugated analyte in a detectable manner;

(c) allowing the sample to flow through a terminal site downstream from the sequential reagent zones and comprising an indicator reagent for confirming the completion of the respective assay, (d) determining the presence of each analyte in the sample by detecting the presence of the respective analyte-conjugate in each readout zone, and assessing the positive and negative controls in each flow path in order to determine the proper performance of the respective assay.

What is claimed is:

1. A device for performing a competitive immunoassay to provide a positive readout for the presence of a monoepitopic or polyepitopic analyte in a sample, the device comprising a bibulous material providing one or more flow paths, each flow path comprising:

(a) a common origin site on the bibulous material for receiving a fluid sample, (b) a plurality of reagent zones emanating from the origin site and providing the reagents necessary for performing a visual readout, competitive immunoassay for the presence of the respective analyte, the zones comprising, in order and in the direction of flow:

(i) a competition zone in fluid communication with the origin site and comprising a detectable analyte-conjugate and binding partner for the analyte, both being diffusively positioned in such a manner that free analyte present in the sample is capable of binding to the binding partner in a competitive manner with the analyte-conjugate;

(ii) a retention zone in fluid communication with the competition zone and comprising an excess amount of a nondiffusively bound capture reagent capable of binding to free or bound binding partner in order to remove it from continued flow in the flow path; and (iii) a readout zone in fluid communication with the retention zone and comprising nondiffusively bound receptor capable of binding in a detectable manner to a conjugate of analyte and label but not capable of binding to unconjugated analyte.

2. A device according to claim 1 further comprising one or more positive and/or negative procedural control zones and reagents in fluid communication with one or more of the reagent zones.

3. A device according to claim 2 wherein the positive control zone comprises a terminal site downstream from the sequential reagent zones and comprising an indicator reagent for confirming the completion of the respective assay.

4. A device according to claim 1 further comprising an inert holder comprising top and bottom portions for supporting the bibulous material, the top portion providing an opening for fluid sample access to the common origin site, as well as openings for viewing the respective readout and terminal indicator sites along each flow path.

5. A device according to claim 1 wherein the analyte is selected from the group consisting of tetrahydrocannabinol, cocaine, opiates, and amphetamines.

6. A method of performing a competitive immunoassay to provide a positive readout for the presence of a monoepitopic or polyepitopic analyte in a sample, the method comprising the steps of:

(a) providing a device comprising a bibulous material having an origin site and one or more flow paths each comprising respective reagent zone providing the reagents necessary for performing a visual readout, competitive immunoassay for the presence of the respective analyte, (b) and applying an aqueous sample to the origin site, (c) allowing the sample to simultaneously flow through each flow path and sequentially through the respective reagent zone providing the reagents necessary for performing a visual readout, competitive immunoassay for the presence of the respective analyte, the zones comprising, in order and in the direction of flow:

(i) a competition zone in fluid communication with the origin site and comprising a detectable analyte-conjugate and binding partner for the analyte, both being diffusively positioned in such a manner that any free analyte present in the sample is capable of binding to the binding partner in a competitive manner with the analyte conjugate;

(ii) a retention zone in fluid communication with the competition zone and comprising an excess amount of a nondiffusively bound capture reagent capable of binding to free or bound binding partner in order to remove it from continued flow in the flow path; and (iii) a readout zone in fluid communication with the retention zone and comprising nondiffusively bound receptor capable of binding in a detectable manner to a conjugate of analyte and label but not capable of binding to unconjugated analyte;

(d) allowing the sample to flow through a terminal site downstream from the sequential reagent zones and comprising an indicator reagent for confirming the completion of the respective assay, (e) determining the presence of the analyte in the sample by detecting the presence of the respective analyte-conjugate in each readout zone, and assessing the completion of the assay in each flow path in order to determine the proper performance of the respective assay.

7. A device for simultaneously performing a plurality of competitive immunoassays to provide a positive readout for the presence of respective analytes in a sample, the device comprising a unitary bibulous material providing one or more flow paths, each flow path comprising:

(a) a common origin site on the bibulous material for receiving a fluid sample, (b) a plurality of respective reagent zones downstream from the origin, the reagent zones of each immunoassay providing the reagents necessary for performing a visual readout, competitive immunoassay for the presence of the respective analyte, the zones comprising, in order and in the direction of flow:

(i) a competition zone comprising a detectable analyte-conjugate and binding partner for the analyte, both being diffusively positioned in such a manner that any free analyte present in the sample is capable of binding to the binding partner in a competitive manner with the analyte conjugate;

(ii) a retention zone comprising an excess amount of a nondiffusively bound capture reagent capable of binding to free or bound binding partner in order to remove it from continued flow in the flow path; and (iii) a readout zone comprising nondiffusively bound receptor capable of binding in a detectable manner to a conjugate of analyte and label but not capable of binding to unconjugated analyte.

8. A device according to claim 7 further comprising one or more positive and/or negative procedural control zones and reagents in fluid communication with one or more of the reagent zones.

9. A device according to claim 8 wherein the positive control zone comprises a terminal site downstream from the sequential reagent zones and comprising an indicator reagent for confirming the completion of the respective assay.

10. A device according to claim 7 further comprising an inert holder comprising top and bottom portions for supporting the bibulous material, the top portion providing an opening for fluid sample access to the common origin site, as well as openings for viewing the respective readout and terminal indicator sites along each flow path.

11. A device according to claim 7 wherein the device provides a separate, discrete flow path for each analyte, the flow paths being positioned to extend in a radial direction from the common origin.

12. A device according to claim 7 wherein the assay is capable of differentially detecting the presence of two or more drugs in a single sample of urine or serum.

13. A device according to claim 12 wherein the analytes are selected from the group consisting of tetrahydrocannabinol, cocaine, opiates, and amphetamines.

14. A device according to claim 7 wherein a spacer moiety is used to conjugate the analyte to the label, and the nondiffusively bound receptor is capable of binding to the spacer moiety.

15. A device according to claim 14 wherein the label comprises a colloidal metal particle.

16. A method for simultaneously performing a plurality of competitive immunoassays to detect the presence of respective monoepitopic or polyepitopic analytes in a sample, the method comprising the steps of providing a device comprising:

(a) a common origin site on the bibulous material for receiving a fluid sample, (b) a plurality of respective reagent zones downstream from the origin, the reagent zones of each immunoassay providing the reagents necessary for performing a visual readout, competitive immunoassay for the presence of the respective analyte, the zones comprising, in order and in the direction of flow:

(i) a competition zone comprising a detectable analyte-conjugate and binding partner for the analyte, both being diffusively positioned in such a manner that any free analyte present in the sample is capable of binding to the binding partner in a competitive manner with the analyte conjugate;

(ii) a retention zone comprising an excess amount of a nondiffusively bound capture reagent capable of binding to free or bound binding partner in order to remove it from continued flow in the flow path; and (iii) a readout zone comprising nondiffusively bound receptor capable of binding in a detectable manner to a conjugate of analyte and label but not capable of binding to unconjugated analyte, wherein the method comprises the steps of:

(a) applying an aqueous sample to the unitary bibulous material at a common origin site of one or more flow paths, (b) allowing the sample to simultaneously flow through each flow path and sequentially through a plurality of respective reagent zones providing the reagents necessary for performing a visual readout, competitive immunoassay for the presence of the respective analyte.

17. A method according to claim 16 wherein the method is capable of simultaneously performing a plurality of immunoassays to detect the presence of respective analytes in a sample, wherein the presence of increasing amounts of free analyte in a sample leads to the binding of less analyte-conjugate to the binding partner.

* * * * *